United States Patent [19]

Carpenter

[11] Patent Number: 5,674,517
[45] Date of Patent: Oct. 7, 1997

US005674517A

[54] EMULSIFIER FOR PESTICIDE CONCENTRATES

[75] Inventor: Dale A. Carpenter, West Chester, Ohio

[73] Assignee: Henkel Corporation, Plymouth Meeting, Pa.

[21] Appl. No.: 638,422

[22] Filed: Apr. 26, 1996

[51] Int. Cl.$^6$ ................................................. A01N 25/00
[52] U.S. Cl. ...................................................... 424/405
[58] Field of Search .................... 424/409, 405; 568/23, 716

[56] References Cited

U.S. PATENT DOCUMENTS

| | | | |
|---|---|---|---|
| 4,029,817 | 6/1977 | Blanco et al. | 424/78.04 |
| 4,770,694 | 9/1988 | Iwasaki et al. | 71/93 |

OTHER PUBLICATIONS

Chem. Ab. 111: 148930 W. Smith et al 1989.
Chem. Ab. 79: 2829L Abbott et al 1973.
Chem. Ab. 116:230224 Sato et al. 1992.
Chem. Ab. 109:94897 Kato et al. 1988.

*Primary Examiner*—Peter F. Kulkosky
*Attorney, Agent, or Firm*—Wayne C. Jaeschke; John E. Drach; Steven J. Trzaska

[57] ABSTRACT

An emulsifier for emulsifying pesticide concentrates, the emulsifier consisting essentially of: (i) a sulfate as represented by general formula I:

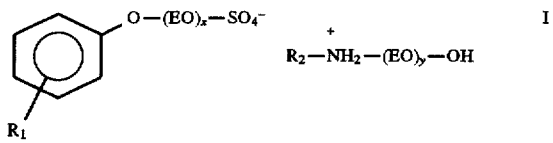

wherein $R_1$ is an alkyl group having 8 or 9 carbon atoms, $R_2$ is an alkyl radical having from 8 to 22 carbon atoms, x is a number from 4 to 10 and, y is a number from 2 to 20; and (ii) a nonionic surfactant selected from the group consisting of alkoxylated block copolymers of $C_{8-12}$ alkylphenols, castor oil ethoxylates, mono- and di-esters of ethylene glycol, ethoxylated $C_{8-22}$ alcohols, sorbitan esters, ethoxylated sorbitan esters, ethylene oxide-propylene oxide block copolymers, propoxylated-ethoxylated butanols, and mixtures thereof.

28 Claims, No Drawings

1

EMULSIFIER FOR PESTICIDE CONCENTRATES

FIELD OF THE INVENTION

The present invention generally relates to an agricultural composition. More particularly, the invention relates to a novel pesticide formulation which allows a pesticide and tributoxyethyl phosphate to be emulsified into a single agricultural composition.

BACKGROUND OF THE INVENTION

It is known that various pesticides such as insecticides, insect repellents, fungicides, bactericides, herbicides, and plant growth regulators may be formulated into various agricultural products for use on crops and ornamental plants, for controlling weeds, insects and the like. These products may be applied in the form of a liquid or a semi-solid dispersion.

The successful employment of any pesticide depends upon its proper formulation in a preparation that can be easily combined with water into ready-to-use form for application onto an agricultural substrate with safety to the applicator, animals and plants. The preparation and use of such formulations typically necessitates making them in concentrated form. Thus, the use of auxiliary agents such as solvents, emulsifiers, wetting and dispersing agents are typically required. The preparation of such pesticide concentrates, however, oftentimes poses certain formulation problems due to the incompatability of the pesticide component with other components combined therewith.

SUMMARY OF THE INVENTION

This invention concerns novel compositions and methods for the treatment of agricultural substrates. It has been surprisingly found that an emulsifier based on a combination of a sulfate and certain nonionic surfactants imparts exceptional emulsifying properties to pesticide concentrates.

The present invention is thus directed to a novel emulsifier for use in formulating pesticide concentrates, the emulsifier consisting essentially of:

(i) a sulfate as represented by general formula I:

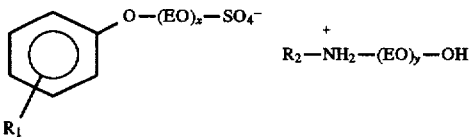

wherein $R_1$ is an alkyl group having 8 or 9 carbon atoms, $R_2$ is an alkyl radical having from 8 to 22 carbon atoms, x is a number from 4 to 10 and, y is a number from 2 to 20; and (ii) a nonionic surfactant selected from the group consisting of alkoxylated block copolymers of $C_{8-12}$ alkylphenols, castor oil ethoxylates, mono- and di-esters of ethylene glycol, ethoxylated $C_{8-22}$ alcohols, sorbitan esters, ethoxylated sorbitan esters, ethylene oxide-propylene oxide block copolymers, propoxylated-ethoxylated butanols, and mixtures thereof.

The present invention is also directed to a pesticide composition containing:

(a) a pesticide selected from the group consisting of insecticides, insect repellents, fungicides, bactericides, bacteriostats, herbicides, plant growth regulators, and mixtures thereof; and (b) an emulsifier containing:

(i) a sulfate as represented by general formula I; and (ii) a nonionic surfactant selected from the group consisting of alkoxylated block copolymers of $C_{8-12}$ alkylphenols, castor oil ethoxylates, mono- and di-esters of ethylene glycol, ethoxylated $C_{8-22}$ alcohols, sorbitan esters, ethoxylated sorbitan esters, ethylene oxide-propylene oxide block copolymers, propoxylated-ethoxylated butanols, and mixtures thereof.

The present invention also provides a process for emulsifying a pesticide composition involving the steps of:

(a) providing a pesticide selected from the group consisting of insecticides, insect repellents, fungicides, bactericides, bacteriostats, herbicides, plant growth regulators, and mixtures thereof; and (b) providing an emulsifier containing:

(i) a sulfate as represented by general formula I; and (ii) a nonionic surfactant selected from the group consisting of alkoxylated block copolymers of $C_{8-12}$ alkylphenols, castor oil ethoxylates, mono- and di-esters of ethylene glycol, ethoxylated $C_{8-22}$ alcohols, sorbitan esters, ethoxylated sorbitan esters, ethylene oxide-propylene oxide block copolymers, propoxylated-ethoxylated butanols, and mixtures thereof; and (c) mixing components (a) and (b) to form an emulsion.

BRIEF DESCRIPTION OF THE INVENTION

Other than in the operating examples, or where otherwise indicated, all numbers expressing quantities of ingredients or reaction conditions used herein are to be understood as being modified in all instances by the term "about".

The present invention is based on the surprising discovery that an emulsifier based on a sulfate as represented by general formula I in combination with certain nonionic surfactants, imparts superior emulsifying properties to pesticide concentrates.

The sulfates according to the invention are compounds of the formula I:

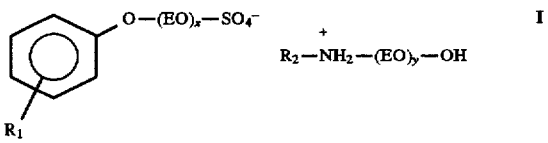

wherein $R_1$ is an alkyl group having 8 or 12 carbon atoms, $R_2$ is an alkyl radical having from 8 to 22 carbon atoms, x is a number from 1 to 10 and, y is a number from 2 to 60. Preferably, $R_1$ is an alkyl group having 9 carbon atoms, $R_2$ is an alkyl or alkenyl group having 16 to 18 carbon atoms or a mixture of such alkyl and alkenyl groups. It is particularly preferred for $R_2$ to be derived from tallow alcohol which contains from about 45% to about 55% by weight of a mixture of saturated fatty alcohols a majority of which are stearyl and palmityl alcohols and from about 45% to about 55% by weight of a mixture of unsaturated fatty alcohols a large majority of which is oleyl alcohol and which may also contain linoleyl and linolenyl alcohols. It is also preferred that x have a value of from 1 to 10 and that y have a value of from 3 to 60. A particularly preferred sulfate is typically known as tallowamine POE(5) salt of nonylphenol POE(4) sulfate.

The nonionic surfactants suitable for use in the emulsifier are selected from the group consisting of alkoxylated block copolymers of $C_{8-12}$ alkylphenols, castor oil ethoxylates, mono- and di-esters of ethylene glycol, ethoxylated $C_{8-22}$ alcohols, sorbitan esters, ethoxylated sorbitan esters, ethylene oxide-propylene oxide block copolymers, propoxylated-ethoxylated butanols, and mixtures thereof.

The alkoxylated $C_{8-12}$ alkylphenols are typically represented as $C_{8-12}$ alkyphenol POP(20–40)POE(20–60) block copolymers. A particularly preferred example thereof is a nonylphenol POP(30)POE(40) block copolymer.

The castor oil ethoxylates useful as nonionics in the present invention are generally derived by ethoxylating castor oil with from 20–55 polyoxyethylene moieties. A particularly preferred example thereof is castor oil POE(36).

The novel emulsifier of the present invention typically contains from about 20 to about 75, and preferably from about 40 to about 60% by weight of the sulfate of formula I, in combination with from about 5 to about 40, and preferably from about 15 to about 30% by weight of the disclosed nonionic surfactants, all weights being based on the total weight of the emulsifier.

In a particularly preferred embodiment, the emulsifier contains from about 40 to about 80% by weight of a $C_{8-22}$ fatty amine POE(3–60) salt of $C_{8-12}$ alkylphenol POE(1–10) sulfate, from about 10 to about 50% by weight of a $C_{8-12}$ alkylphenol POP(20–40) POE(20–60) block copolymer, and from about 2 to about 50% by weight of a castor oil POE(20–55) ethoxylate, all weights being based on the total weight of the emulsifier.

According to another aspect of the present invention, there is provided a pesticide concentrate containing a pesticide in combination with the above-disclosed emulsifier.

The pesticides which can be used to make compositions according to the invention include, but are not limited to insecticides such as O,O-diethyl O-(2-isopropyl-4-methyl-6-pyrimidinyl)phosphorothioate, O,O-diethyl S-2-[(ethylthio)ethyl]phosphorodithioate, O,O-dimethyl O-(3-methyl-4-nitrophenyl)thiophosphate, O,O-dimethyl S-(N-methylcarbamoylmethyl)phosphorodithioate, O,O-dimethylS-(N-methyl-N-formylcarbamoylmethyl) phosphorodithioate, O,O-dimethyl S-2-[(ethylthio)ethyl] phosphorodithioate, O,O-diethyl S-2-[(ethylthio)ethyl] phosphorodithioate, O,O-dimethyl-1-hydroxy-2,2,2-trichloroethylphosphonate, O,O-diethyl-O-(5-phenyl-3-isooxazolyl)phosphorothioate, O,O-dimethyl O-(2,5-dichloro-4-bromophenyl)phosphorothioate, O,O-dimethyl-O-)3-methyl-4-methylmercaptophenyl)thiophosphate, O-ethyl O-p-cyanophenyl-O-phenylphosphorothioate, O,O-dimethyl-S-(1,2-dicarboethoxyethyl)phosphorodithioate, 2-chloro-(2,4,5-trichlorophenyl)vinyldimethyl phosphate, 2-chloro-1 -(2,4-dichlorophenyl)vinyldimethyl phosphate, O,O-dimethyl O-p-cyanophenyl phosphorothioate, 2,2-dichlorovinyl dimethyl phosphate, O,O-diethyl O-2,4-dichlorophenyl phosphorothioate, ethyl mercaptophenylacetate O,O-dimethyl phosphorodithioate, S-[(6-chloro-2-oxo-3-benzooxazolinyl)methyl]O,O-diethyl phosphorodithioate, 2-chloro-1 -(2,4-dichlorophenyl)vinyl diethylphosphate O,O-diethyl O-(3-oxo-2-phenyl-2H-pyridazine-6-yl) phosphorothioate, O,O-dimethyl S-(1 -methyl-2-ethylsulfinyl)-ethyl phosphorothiolate, O,O-dimethyl S-phthalimidomethyl phosphorodithioate, O,O-diethyl 2,2, 2-trichloroethanol, 2-(p-tert-butyl-phenoxy)isopropyl-2'-chloroethylsulfite, azoxybenzene, di-(p-chlorophenyl)-cyclopropyl carbinol, di[tri(2,2-dimethyl-2-phenylethyl)tin] oxide, 1-(4-chlorophenyl)-3-(2,6-difluorobenzoyl)urea and S-tricyclohexyltin O,O-diisopropylphosphorodithioate; 2-methyl-2-(methylthio)propionaldehyde O-(mehtylcarbamoyl)oxime; ethyl [2-(4-phenoxyphenoxy) ethyl] carbamate; butyl-2,3-dihydro-2,2-dimethylbenzofuran-7-yl N,N'-dimethyl-N,N'-thiodicarbamate; 1-naphthyl methyl carbamate; 2-(ethylthiomethyl)phenyl methylcarbamate; 5-(4-phenoxybutyl)dimethylthiocarbamate; dimethyl N,N'-(thiobis(methylimino)carbonyloxy)-bis(ethanimidothioate); (RS)-α-cyano-3-phenoxybenzyl-(RS)-2-(4-chlorophenyl)-3-methylbutyrate; (RS)-α-cyano-3-phenoxyphenyl-(RS)-2, 2-dichloro-1-(4-ethoxyphenyl)cyclopropanecarboxylate; (RS)-α-cyano-3-phenoxybenzyl-N-(2-chloro-α,α,α-trifluoro-p-tolyl-D-valinate; 3-phenoxybenzyl-(1RS)-cis, trans-3-(2,2-dichlorovinyl)-2,2-diemthylcyclopropanedicarboxylate.

Insect repellents which may also be employed include but are not limited to 2-ethyl-1,3-hexanediol; N-octyl bicycloheptene dicarboximide; N,N-diethyl-M-toluamide; 2,3:4,5-Bis (2-butylene) tetrahydro-2-furaldehyde; Di-n-propyl isocinchomeronate; and 2-hydroxyethyl-n-octyl sulfide.

Fungicides which may also be employed include but are not limited to 3,3'-ethylenebis (tetrahydro-4,6-dimethyl-2H-1,3,5-thiadiazine-2-thione), zinc or manganese ethylenebis (dithiocarbamate), bis-(dimethyldithiocarbamoyl)disulfide, zinc propylenebis (dithiocarbamate), bis (dimethyldithiocarbamoyl) ethylenediamine; nickel dimethyldithiocarbamate, methyl-1(butylcarbamoyl)-2-benzimidazolecarbamate, 1,2-bis(3-methoxycarbonyl-2-thioureido)benzene, 1-isopropylcarbamoyl-3-(3,5-dichlorophenyl)hydantoin, potassium N-hydroxymethyl-N-methyldithiocarbamate and 5-methyl-10-butoxycarbonylamino-10, 11-dehydrodibenzo (b,f)azepine; pyridine fungicides such as zinc bis(1-hydroxy-2(1H) pyridinethionate and 2-pyridinethiol-1-oxide sodium salt; O,O-diisopropyl S-benzylphosphorothioate and O-ethyl S,S-diphenyldithiophosphate; phthalimide fungicides such as N-(2,6-p-diethylphenyl)phthalimide and N-(2,6-diethylphenyl)-4-methylphthalimide; dicarboxyimide fungicides such as N-trichloromethylthio 4-cyclohexene-1,2-dicarboxyimide and N-tetrachloroethylthio-4-cyclohexene-1,2-dicarboxyimide; 5,6-dihydro-2-methyl-1,4-oxathine-3-carboxanilido-4,4-dioxide and 5,6-dihydro-2-methyl-1, 4-oxathine-3-carboxanilide; naphthoquinone fungicides such as 2,3-dichloro-1,4-naphthoquinone, 2-oxy-3-chloro-1, 4-naphthoquinone copper sulfate, pentachloronitrobenzene; 1,4-dichloro-2,5-dimethoxybenzene; 5-methyl-s-triazol-(3, 4-b)benzthiazole; 2-(thiocyanomethylthio)benzothiazole; 3-hydroxy-5-methylisooxazole; N-2,3-dichlorophenyltetrachlorophthalamic acid; 5-ethoxy-3-trichloromethyl-1,2,4-thiaziazole; 2,4-dichloro-6-(O-chloroanilino)-1,3,5-triazine; 2,3-dicyano-1,4-dithioanthraquinone; copper 8-quinolinate; polyoxine; validamycin; cycloheximide; iron methanearsonate; diisopropyl 1,3-dithiolane-2-iridene malonate; 3-allyloxy-1,2-benzoisothiazol-1,1 -dioxide; kasugamycin; Blasticidin S; 4,5,6,7-tetrachlorophthalide; 3-(3,5-dichlorophenyl)5-ethenyl5-methyloxazolizine-2,4-dione; N-(3,5-dichlorophenyl)-1,2-dimethylcyclopropane-1,2-dicarboxyimide; S-n-butyl-5'-para-t-butylbenzyl-N-3-pyridyldithiocarbonylimidate; 4-chlorophenoxy-3,3-dimethyl-1-(1H, 1,3,4-triazol-1-yl)-2-butanone; methyl-D, L-N-(2,6-dimethylphenyl)-N-(2'-methoxyacetyl)alaninate; N-propyl-N-[2-(2,4,6-trichlorophenoxy)ethyl]imidazol-1-carboxamide; N-(3,5-dichlorophenyl)succinamide; tetrachloroisophthalonitrile; 2-dimethylamino-4-methyl-5-n-butyl-6-hydroxypyrimidine; 2,6-dichloro-4-nitroaniline; 3-methyl-4-chlorobenzthiazol-2-one; 1,2,5,6-tetrahydro-4H-pyrrolol-[3,2,1-i,j]quinoline-2-one; 3'-isopropoxy-2-methylbenzanilide; 1-[2-(2,4-dichlorophenyl)-4-ethyl-1,3- dioxorane-2-ylmethyl]-1H, 1,2,4-triazol; 1,2-benzisothiazoline-3-one; basic copper chloride; basic copper sulfate; N'-dichlorofluoromethylthio-N,N-dimethyl-N-phenyl sulfamide; ethyl-N-(3-dimethylaminopropyl) thiocarbamate hydrochloride; piomycin; S,S-6-methylquinoxaline-2,3-di-yldithiocarbonate; complex of zinc and manneb; di-zinc bis(dimethyldithiocarbamate) ethylenebis (dithiocarbamate).

Plant growth regulators which may also be employed include but are not limited to N-methoxycaronyl-N'-4-methylphenylcarbamoylethylisourea and 1-(4-chlorophenylcarbamoyl)-3-ethoxycarbonyl-2-methylisourea; another type of plant growth regulators such as sodium naphthaleneacetate, 1,2-dihydropyridazine-3,6-dione and gibberellins; traizine herbicides such as 2-methylthio-4,6-bisethylamino-1,3,5-triazine, 2-chloro-4, 6-bisethylamino-1,3,5-triazine, 2-methoxy-4-ethylamino-6-isopropylamino-1,3,5-triazine, 2-chloro-4-ethylamino-6-isopropylamino-s-triazine, 2-methylthio-4,6-bis (isopropylamino)-S-triazine and 2-methylthio-4-ethylamino-6-isopropylamino-s-triazine; phenoxy herbicides such as 2,4-dichlorophenoxyacetic acid and methyl, ethyl, and butyl esters thereof. 2-chloro-4-methylphenoxyacetic acid, 4-chloro-2-methylphenoxyacetic acid and ethyl 2-methyl-4-chlorophenoxybutylate; diphenylether herbicides such as 2,4,6-trichlorophenyl-4'-nitrophenylether, 2,4-dichlorophenyl-4'-nitrophenylether and 3,5-dimethylphenyl-4'-nitrophenylether; urea herbicides such as 3-(3,4-dichlorophenyl)-1-methoxy-1-methyl urea, 3-(3,4-dichlorophenyl)-1,1-dimethylurea and 3-(4-chlorophenyl)-1,1-dimethyl urea; carbamate herbicides such as 3-methoxycarbonylaminophenyl-N-(3-methylphenyl) carbamate, isopropyl-N-(3-chlorophenyl)carbamate and methyl-N-(3,4'-dichlorophenyl)carbamate; uracil herbicides such as 5-bromo-3-sec-butyl-6-methyluracil and 1-cyclohexyl-3,5-propyleneuracil; thiolcarbamate herbicides such as S-(4-chlorobenzyl)-N,N-diethylthiolcarbamate,S-ethyl-N-cyclohexyl-N-ethylthiolcarbamate and S-ethyl-hexahydro-1H-azepine-1-carbothioate and S-ethyl-N,N-di-n-propyl-thiocarbamate; pyridinium herbicides such as 1,1'-di-methyl-4,4'-bispyridinium dichloride; phosphoric herbicides such as N-(phosphonomethyl)glycine; aniline herbicides such as alpha, alpha, alpha-trifluoro-2,6-dinitro-N,N-dipropyl-p-toluidine, 4-(methylsulfonyl)-2,6-dinitro-N,N-dipropylaniline and N[3], N[3]-diethyl-2,4-dinitro-6trifluoromethyl-1,3-phenylene diamine; acid anilide herbicides such as 2-chloro-2',6'-diethyl-N-(butoxymethyl) acetoanilide, 2-chloro-2',6'-diethyl-N-(methoxymethyl) acetoanilide, and 3,4-dichloropropioneanilide; pyrazole herbicides such as 1,3-dimethyl-4-(2,4-dichlorobenzoyl)-5-hydroxypyrazole and 1,3-di-methyl-4-(2,4-dichlorobenzoyl)-5-(p-toluenesulfonyloxy)pyrazole; 5-tert-butyl-3-(2,4-dichloro-5-isopropoxyphenyl)-1,3,4-oxadiazoline-2-one; 2-[N-isopropyl, N-(4-chlorophenyl)carbamoyl]-4-chloro-5-methyl-4-isooxazoline-3-one; 3-isopropylbenzo-2-thia-1,3-diazinone-(4)-2,4-dioxide and 3-(2-methyl-phenoxy) pyridazine.

While the specific pesticide(s) used will be chosed by those skilled in the art depending on their objectives, in a particularly preferred embodiment of the present invention, the pesticide employed is permethrin insecticide.

The pesticide concentrate of the present invention is preferably formulated by combining from about 0.5 to about 50, and most preferably from about 5 to about 40% by weight of a pesticide, and from about 1 to about 40% by weight of the above-disclosed emulsifier, all weights being based on the total weight (100%) of the pesticide concentrate.

In many cases, it is oftentimes desirable to employ a solvent as a carrier for pesticides. The use of a solvent serves to facilitate the effective formulation of a disperse ready-to-use pesticide concentrate. Examples of solvents suitable for use in the present invention include, but are not limited to, tributoxyethyl phosphate, triacetin, tetrahydrofurfuryl alcohol, methyl esters of fatty acids, corn and cotton seed oil and esters thereof, alkyl biphenyls, and aliphatic, alicyclic and aromatic hydrocarbons.

In the event that a solvent is employed as a component of the pesticide concentrate, it is typically present in an amount of from about 1 to about 95% by weight, based on the weight of the pesticide concentrate.

According to one embodiment of the present invention, a pesticide concentrate is provided containing from about 1 to about 90% by weight of permethrin insecticide, from about 1 to about 95% by weight of tributoxyethyl phosphate solvent, and from about 1 to about 40% by weight of the above-disclosed emulsifier, all weights being based on the total weight (100%) of the pesticide concentrate.

In a particularly preferred embodiment of the present invention, there is provided a pesticide concentrate containing: (a) from about 5 to about 40% by weight of a pesticide component, preferably permethrin technical, (b) from about 2 to about 20% by weight of tallowamine POE(5) salt of nonylphenol POE(4) sulfate, (c) from about 1 to about 20% by weight of a nonylphenol POP(30)POE(40) block copolymer, and (d) from about 0.5 to about 10% by weight of castor oil POE(36), all weights being based on the total weight of the composition.

According to another aspect of the present invention, there is also provided a process for emulsifying a pesticide concentrate. This process involves combining from about 0.5 to about 50% by weight, and most preferably from about 5 to about 40% by weight, of the above-disclosed pesticide with from about 1 to about 40% by weight of the above-disclosed emulsifier, all weights being based on the total weight (100%) of the pesticide concentrate. In the event that a solvent is used, it too will be combined with the pesticide concentrate in an amount of from about 1 to about 95% by weight, based on the total weight of the concentrate.

The present invention will be better understood from the example which follow, all of which are intended to be illustrative only and not meant to unduly limit the scope of the invention. Unless otherwise indicated, percentages are on a weight-by-weight basis.

EXAMPLE 1

A pesticide concentrate was prepared per the following formulation:

| Component | %/wt |
|---|---|
| (a) permethrin technical | 37.0 |
| (b) tributoxyethyl phosphate | 54.5 |
| (c) tallowamine POE(5) salt of nonylphenol POE(4) sulfate | 5.0 |
| (d) nonylphenol POP(30)POE(40) block copolymer | 2.5 |
| (e) castor oil POE(36) | 1.0 |
| | 100.0 |

What is claimed is:

1. An emulsifier for emulsifying pesticide concentrates, the emulsifier consisting essentially of:

(i) from about 20 to about 75 percent by weight, based on the emulsifier of a sulfate as represented by general formula I:

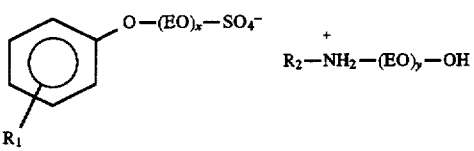

wherein $R_1$ is an alkyl group having 8 or 9 carbon atoms, $R_2$ is an alkyl radical having from 8 to 22 carbon atoms, x is a number from 4 to 10 and, y is a number from 2 to 20; and (ii) a nonionic surfactant selected from the group consisting of alkoxylated block copolymers of $C_{8-12}$ alkylphenols, castor oil ethoxylates, mono- and di-esters of ethylene glycol, ethoxylated $C_{8-22}$-alcohols, sorbitan esters, ethoxylated sorbitan esters, ethylene oxide-propylene oxide block copolymers, propoxylated-ethoxylated butanols, and mixtures thereof.

2. The emulsifier of claim 1 wherein the sulfate of formula I is a tallowamine POE(5) salt of nonylphenol POE(4) sulfate.

3. The emulsifier of claim 1 wherein the nonionic surfactant is a nonylphenol POP(30)POE(40) block copolymer.

4. The emulsifier of claim 1 wherein the nonionic surfactant is a castor oil PO5(36).

5. The emulsifier of claim 1 wherein the sulfate of formula I is present in the emulsifier in an amount ranging from about 40 to about 60 percent by weight, based on the weight of the emulsifier.

6. The emulsifier of claim 1 wherein the nonionic surfactant is present in the emulsifier in an amount ranging from about 5 to about 40% by weight, based on the weight of the emulsifier.

7. The emulsifier of claim 6 wherein the nonionic surfactant is present in the emulsifier in an amount ranging from about 15 to about 30% by weight, based on the weight of the emulsifier.

8. The emulsifier of claim 1 wherein in formula I, $R_2$ is derived from tallow alcohol.

9. The emulsifier of claim 1 consisting essentially of from about 40 to about 80% by weight of a $C_{8-22}$ fatty amine POE(3–60) salt of a $C_{8-12}$ alkylphenol POE(1–10) sulfate, from about 10 to about 50% by weight of a $C_{8-12}$ alkylphenol POP(20–40) POE(20–60) block copolymer, and from about 2 to about 50% by weight of a castor oil POE(20–55) ethoxylate, all weights being based on the weight of the emulsifier.

10. A pesticide composition comprising:
(a) from about 0.5 to about 50% by weight of a pesticide selected from the group consisting of insecticides, insect repellents, fungicides, bactericides, bacteriostats, herbicides, plant growth regulators, and mixtures thereof; and
(b) from about 1 to about 40% by weight of an emulsifier consisting essentially of:
(i) a sulfate as represented by general formula I:

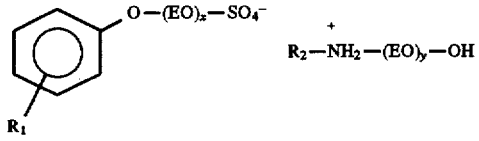

wherein $R_1$ is an alkyl group having 8 or 9 carbon atoms, $R_2$ is an alkyl radical having from 8 to 22 carbon atoms, x is a number from 4 to 10 and, y is a number from 2 to 20; and
(ii) a nonionic surfactant selected from the group consisting of alkoxylated block copolymers of $C_{8-12}$ alkylphenols, castor oil ethoxylates, mono- and di-esters of ethylene glycol, ethoxylated $C_{8-22}$-alcohols, sorbitan esters, ethoxylated sorbitan esters, ethylene oxide-propylene oxide block copolymers, propoxylated-ethoxylated butanols, and mixtures thereof, all weights being based on the weight of the composition.

11. The composition of claim 10, wherein the sulfate of formula I is a tallowamine POE(5) salt of nonylphenol POE(4) sulfate.

12. The composition of claim 10 wherein the nonionic surfactant is a nonylphenol POP(30)POE(40) block copolymer.

13. The composition of claim 10 wherein the nonionic surfactant is a castor oil POE(36).

14. The composition of claim 10 wherein the sulfate of formula I is present in the emulsifier in an amount ranging from about 20 to about 75 percent by weight, based on the weight of the emulsifier.

15. The composition of claim 14 wherein the sulfate of formula I is present in the emulsifier in an amount ranging from about 40 to about 60 percent by weight, based on the weight of the emulsifier.

16. The composition of claim 10 wherein the nonionic surfactant is present in the emulsifier in an amount ranging from about 5 to about 40% by weight, based on the weight of the emulsifier.

17. The composition of claim 16 wherein the nonionic surfactant is present in the emulsifier in an amount ranging from about 15 to about 30% by weight, based on the weight of the emulsifier.

18. The composition of claim 10 further comprising from about 1 to about 95% by weight of a solvent selected from the group consisting of tributoxyethyl phosphate, triacetin, tetrahydrofurfuryl alcohol, methyl esters of fatty acids, corn and cotton seed oil and esters thereof, alkyl biphenyls, and aliphatic, alicyclic and aromatic hydrocarbons.

19. The composition of claim 18 wherein the solvent is tributoxyethyl phosphate.

20. A process for emulsifying a pesticide comprising the steps of:
(a) providing a pesticide selected from the group consisting of insecticides, insect repellents, fungicides, bactericides, bacteriostats, herbicides, plant growth regulators, and mixtures thereof;
(b) providing an emulsifier consisting essentially of:
(i) from about 20 to about 75 percent by weight, based on the emulsifier of a sulfate as represented by general formula I:

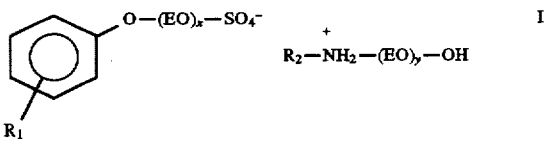

wherein $R_1$ is an alkyl group having 8 or 9 carbon atoms, $R_2$ is an alkyl radical having from 8 to 22 carbon atoms, x is a number from 4 to 10 and, y is a number from 2 to 20; and
(ii) a nonionic surfactant selected from the group consisting of alkoxylated block copolymers of $C_{8-12}$ alkylphenols, castor oil ethoxylates, mono- and di-esters of ethylene glycol, ethoxylated $C_{8-22}$-alcohols, sorbitan esters, ethoxylated sorbitan esters, ethylene oxide-propylene oxide block copolymers, propoxylated-ethoxylated butanols, and mixtures thereof, all weights being based on the weight of the composition; and
(c) mixing components (a) and (b) to form an emulsion.

21. The process of claim 20 wherein the sulfate of formula I is a tallowamine POE(5) salt of nonylphenol POE(4) sulfate.

22. The process of claim 20 wherein the nonionic surfactant is a nonylphenol POP(30)POE(40) block copolymer.

23. The process of claim 20 wherein the nonionic surfactant is a castor oil POE(36).

24. The process of claim 20 wherein the sulfate of formula I is present in the emulsifier in an amount ranging from about 40 to about 60 percent by weight, based on the weight of the emulsifier.

25. The process of claim 20 wherein the nonionic surfactant is present in the emulsifier in an amount ranging from about 5 to about 40% by weight, based on the weight of the emulsifier.

26. The process of claim 25 wherein the nonionic surfactant is present in the emulsifier in an amount ranging from about 15 to about 30% by weight, based on the weight of the emulsifier.

27. The process of claim 20 further comprising adding to the emulsion from about 1 to about 95% by weight of a solvent selected from the group consisting of tributoxyethyl phosphate, triacetin, tetrahydrofurfuryl alcohol, methyl esters of fatty acids, corn and cotton seed oil and esters thereof, alkyl biphenyls, and aliphatic, alicyclic and aromatic hydrocarbons.

28. The process of claim 27 wherein the solvent is tributoxyethyl phosphate.

* * * * *